United States Patent [19]

Hiltebrandt

[11] Patent Number: 5,112,321
[45] Date of Patent: May 12, 1992

[54] TROCAR SLEEVE HAVING MANUAL CLOSURE

[75] Inventor: Siegfried Hiltebrandt, Knittlingen, Fed. Rep. of Germany

[73] Assignee: Richard Wolf GmbH, Knittlingen, Fed. Rep. of Germany

[21] Appl. No.: 712,359

[22] Filed: Jun. 7, 1991

[51] Int. Cl.⁵ .............................................. A61M 5/00
[52] U.S. Cl. .................................. 604/264; 604/167
[58] Field of Search ............... 604/167, 164, 264, 158, 604/93, 284

[56] References Cited

U.S. PATENT DOCUMENTS

| 4,112,932 | 9/1978 | Chiulli | 604/264 X |
| 4,769,005 | 9/1988 | Ginsburg et al. | 604/264 X |

FOREIGN PATENT DOCUMENTS

| 7004051 | 7/1970 | Fed. Rep. of Germany . |
| 7220273 | 2/1973 | Fed. Rep. of Germany . |
| 7736389 | 3/1978 | Fed. Rep. of Germany . |
| 2716774 | 10/1978 | Fed. Rep. of Germany . |
| 1356386 | 6/1974 | United Kingdom . |
| 1482857 | 8/1977 | United Kingdom . |
| 2012919 | 8/1979 | United Kingdom . |

Primary Examiner—John J. Wilson
Assistant Examiner—Jeffrey A. Smith
Attorney, Agent, or Firm—Cohen, Pontani, Lieberman & Pavane

[57] ABSTRACT

The invention relates to a trocar sleeve for guiding endoscopes and instruments which can be exchanged for a trocar, the tube of the trocar sleeve being connected proximally to a handle part and being closable. The proximal end face of the handle part is covered by a closure part which can be adjusted by hand transversely to the tube axis and has at least one hole with an introduction support connected to it. The or each hole of the closure part can be covered by the tube channel as a result of appropriate rotation of the closure part.

6 Claims, 1 Drawing Sheet

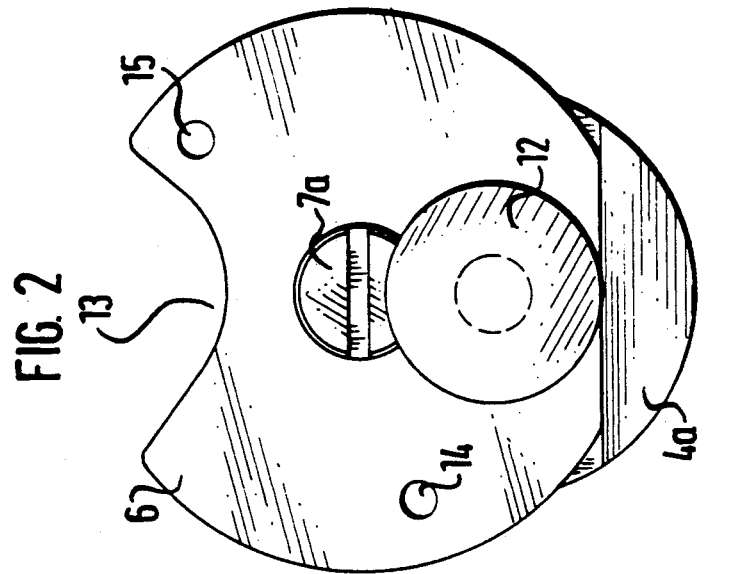
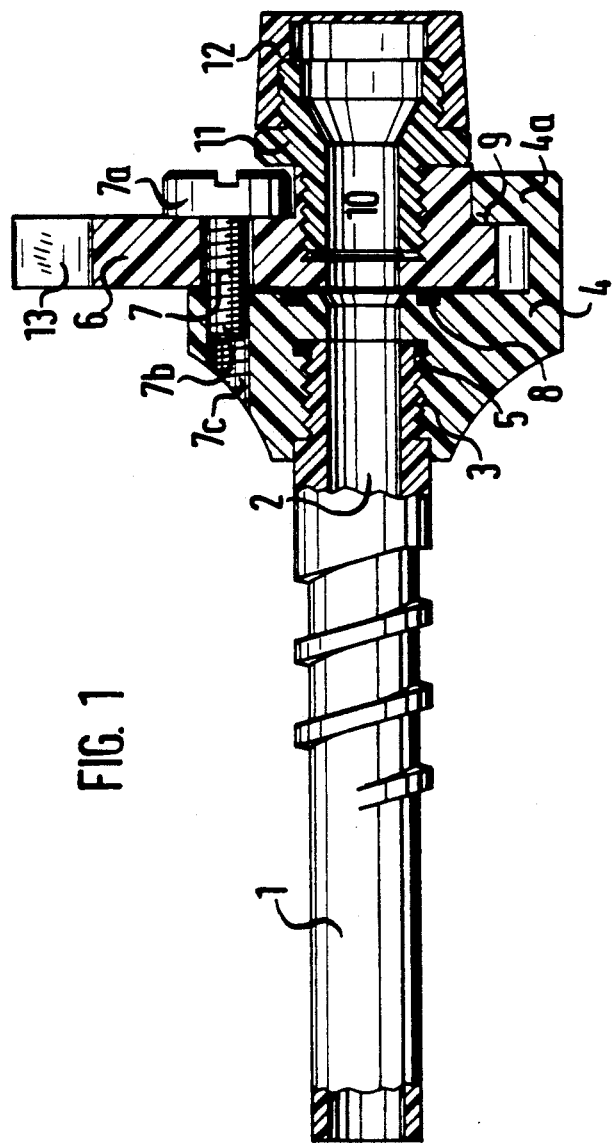

TROCAR SLEEVE HAVING MANUAL CLOSURE

BACKGROUND OF THE INVENTION (a) Field of the Invention

The invention relates to a trocar sleeve for guiding endoscopes and operation instruments which can be exchanged for a trocar, it being possible for the tube of the trocar sleeve to be connected proximally to a handle part and to be closed in a gas-tight manner.

(b) Description of the Prior Art

Known trocar sleeves have conventional ball valves, trumpet valves or solenoid valves to close the central tube channel of the trocar sleeve before introducing or after removing a guided endoscope, an auxiliary instrument or the like, in a gas-tight manner. Trocar sleeves of this type are disclosed in the following references: German Gebrauchsmuster Nos. 70 04 051, 72 20 273, 74 30 345, 77 35 963 and 77 36 389.

A disadvantage of known trocar sleeves is that the closing element is biased by a spring, as a result of which the endoscopes or instruments are engaged at their outer surfaces and therefore their free movement and guidance is braked or otherwise restricted. Engagement of the instruments may have a disadvantageous effect on their operability or may even render the instruments unusable. Furthermore, since trocar sleeves generally consist of metal, this may have an interfering effect when taking X-rays, since organs of the body may be covered by the sleeve. Also, when changing the instrument, loss of gas may occur during introduction or removal.

The principal objects of the invention are to avoid the abovementioned disadvantages of known trocar sleeves, to be able to introduce endoscopes and instruments through the trocar sleeve into the body cavity unhindered by friction and to be able to use instruments and endoscopes of different diameter or cross-sectional profile.

SUMMARY OF THE INVENTION

With these objects in view, the present invention provides a trocar sleeve for guiding endoscopes and instruments which can be exchanged for a trocar, the tube of the trocar sleeve being connectable proximally to a handle part and being closable, characterized in that the proximal end face of the handle part is covered by a closure part which can be adjusted transversely to the tube axis and has at least one hole with an introduction support connected proximally to the closure part, and in that the hole can be covered by the tube channel.

Preferably, the closure part is a disc and can be rotated about a fastening pin on the handle part parallel to the tube axis, so that the closure disc is aligned with a hole and the tube channel.

The closure part may be provided with two stop pins on the distal side which come to rest against the periphery of the handle part when the disc is rotated and define the end positions of the closure part.

In an advantageous embodiment of the invention, the closure part is retained against the proximal end face of the handle part on one side of the tube channel by means of the fastening pins and is retained against the proximal end face of the handle part on the side opposite the tube channel by means of a projection on the handle part.

The handle part is suitably sealed from the closure part by means of a sealing ring inserted in an annular groove of the handle part.

The closure part may be provided with a peripheral recess between the two stop pins, for finger engagement.

In a preferred arrangement, the closure part as a slide is provided with a hole and connecting introduction support, and is retained against the proximal end face of the handle part guided transversely, the displacement in opposite directions being limited by means of stops, with the tube channel being either closed or aligned with the hole in the slide when the slide is in the stop position.

BRIEF DESCRIPTION OF THE DRAWINGS

In order that the invention may be more readily understood, an embodiment of the invention will now be described, by way of example only, with reference to the accompanying drawings in which:

FIG. 1 shows a side view of a trocar sleeve according to the invention with proximal and distal axial section;

FIG. 2 shows a view in the direction towards the proximal end of the trocar sleeve according to FIG. 1.

DETAILED DESCRIPTION OF A PRESENTLY PREFERRED EMBODIMENT

The trocar sleeve according to the invention comprises a tube 1 with a diameter widening slightly in the proximal direction and having central channel 2 and a handle 4 which can be connected to the tube 1 by means of a screw fitting 3. The seal between the proximal tube end and the handle part 4 is made by means of an inserted sealing ring 5.

A closure disc 6 lies against the proximal end face of the handle part 4. This closure disc 6 is engaged by a pin 7 parallel to the tube axis with slight clearance, which pin 7 can be screwed into a threaded bore 7c in the handle part 4 by means of a screw head 7a having a thread end 7b, as a result of which the closure disc 6 is retained in a sealing manner against the proximal end face of the handle part. A faultless seal is made by means of a sealing ring 8 inserted in an annular groove in the handle part 4. In order to achieve as even a support as possible for the closure disc 6 at the end face of the handle part 4, the handle part 4 is provided with a projection 4a on the side opposite the fastening pin 7, which projection 4a rests against a shoulder 9 on the closure disc 6.

The closure disc 6 can be rotated about the pin 7 in two directions, so that its hole 10 can be covered by the tube channel 2 by rotating the closure disc 6 in one direction. An introduction support 11 for the instruments to be guided is provided at the hole 10, and a seal bonnet 12 is placed on it.

The closure disc 6 provided with a peripheral recess 13 for engagement of a finger can be rotated clockwise and anticlockwise into two positions. The disc 6 is rotated in the clockwise direction until a tube-side pin 15 on the disc 6 abuts against the periphery of the handle part 4. The tube channel 2 is then closed in a gas-tight manner by means of the closure disc 6. In the opposite direction of rotation a pin 14 comes to rest against the periphery of the handle part 4. In this stop position the hole 10 in the closure disc is covered by the tube channel 2, so that instruments can be introduced into a body cavity through the trocar sleeve in this position.

It is also possible to provide the closure disc 6 with several holes 10 of different diameter and corresponding introduction supports in order to attach adaptation elements, for example next to a hole for instruments, to which an endoscope camera or even a pressure measuring device or the like can be connected.

A closure slide, which can be moved guided by hand transversely to the tube axis at the proximal surface of the handle part, and can be moved into a position closing the tube channel and into one or more positions in which one single hole of several holes can be covered by the tube channel, may also be used instead of the rotatable closure disc. These positions may be fixed by means of stops.

Whilst a particular embodiment has been described, it should be appreciated that the invention is not limited thereto but includes all modifications and variations falling within its scope.

What is claimed is:

1. An apparatus for guiding a medical instrument into a body cavity comprising:
   a trocar sleeve comprising an elongated tube forming a channel and having an axis and a proximal and distal end;
   a handle part connected to said proximal end of said sleeve, said handle part comprising a handle part opening in axial alignment with said tube channel and a proximal end face, and a U-shaped projection;
   a closure part formed as a disc having at lest one closure part opening therein and being movably mounted on said proximal end face of said handle part, said closure part comprising means for introducing said medical instrument through said tube and said channel and being movable transversely to said sleeve axis from a first position wherein said closure part seals said tube channel to a second position wherein said closure part opening is in axial alignment with said tube channel for permitting the insertion of said instrument; and
   a fastening pin being opposite said U-shaped projection and extending parallel to said sleeve axis through said disc into said handle part for permitting said movement of said disc thereabout, wherein said closure part is retained against said proximal end face of said handle part on one side of said tube channel by means of said fastening pin and is retained against said proximal end face on the opposite side of said tube channel by means of said projection.

2. The apparatus of claim 1, additionally comprising two stop pins at said closure part extending parallel to said tube channel toward said distal end of said sleeve so as to come to rest against said handle part for limiting said movement of said closure part.

3. The apparatus of claim 1, additionally comprising a seal between said handle part and said closure part.

4. The apparatus of claim 3, additionally comprising a circular groove for housing said seal in said handle part around said handle part opening.

5. The apparatus of claim 1, additionally comprising a peripheral recess in said closure part for finger engagement.

6. The apparatus of claim 5, wherein said peripheral recess is located between said stop pins and opposite said projection.

* * * * *